(12) United States Patent
Meacham et al.

(10) Patent No.: US 10,807,029 B2
(45) Date of Patent: Oct. 20, 2020

(54) HIGH THROUGHPUT ACOUSTIC PARTICLE SEPARATION METHODS AND DEVICES

(71) Applicant: Washington University, St. Louis, MO (US)

(72) Inventors: John Mark Meacham, St. Louis, MO (US); Michael Binkley, St. Louis, MO (US); Andrei G. Fedorov, St. Louis, MO (US); Fahrettin Levent Degertekin, St. Louis, MO (US); Courtney Swadley, St. Louis, MO (US)

(73) Assignee: WASHINGTON UNIVERSITY, St. Louis, MO (US)

( * ) Notice: Subject to any disclaimer, the term of this patent is extended or adjusted under 35 U.S.C. 154(b) by 108 days.

(21) Appl. No.: 16/085,314

(22) PCT Filed: Mar. 15, 2017

(86) PCT No.: PCT/US2017/022484
§ 371 (c)(1),
(2) Date: Sep. 14, 2018

(87) PCT Pub. No.: WO2017/160964
PCT Pub. Date: Sep. 21, 2017

(65) Prior Publication Data
US 2019/0076769 A1 Mar. 14, 2019

Related U.S. Application Data

(60) Provisional application No. 62/308,547, filed on Mar. 15, 2016.

(51) Int. Cl.
*B01D 43/00* (2006.01)
*B01D 21/28* (2006.01)
(Continued)

(52) U.S. Cl.
CPC .......... *B01D 43/00* (2013.01); *B01D 21/283* (2013.01); *B06B 1/0607* (2013.01); *C12M 47/04* (2013.01)

(58) Field of Classification Search
CPC ...... B01D 21/00; B01D 21/28; B01D 21/283; B01D 43/00; B06B 1/00; B06B 1/02;
(Continued)

(56) References Cited

U.S. PATENT DOCUMENTS

2015/0321129 A1 11/2015 Lipkens et al.

FOREIGN PATENT DOCUMENTS

RU 2480522 C2 4/2013

OTHER PUBLICATIONS

International Search Report and Written Opinion issued in PCT/US2017/022484 dated Jun. 29, 2017.
(Continued)

*Primary Examiner* — Natasha E Young
(74) *Attorney, Agent, or Firm* — Armstrong Teasdale LLP

(57) ABSTRACT

Disclosed herein are devices and methods of high throughput separation. A device comprises a reservoir for receiving a fluid in a flow direction and a transducer for generating a pressure field that is not perpendicular to the flow direction of the fluid through the reservoir. A method comprises receiving a fluid in a flow direction into a reservoir comprising an array of openings on at least one side of the channel or reservoir, generating a pressure field that is not perpendicular to the flow of the fluid through the reservoir, wherein at least one node and at least one antinode of the pressure field are within the reservoir, and separating the plurality of objects within the fluid, wherein at least a first object is retained within the reservoir and at least a second object is passed from the reservoir through the array of openings.

25 Claims, 14 Drawing Sheets

(51) Int. Cl.
*C12M 1/00* (2006.01)
*B06B 1/06* (2006.01)

(58) Field of Classification Search
CPC ........ B06B 1/06; B06B 1/0607; C12M 47/00; C12M 47/04
See application file for complete search history.

(56) References Cited

OTHER PUBLICATIONS

Li Peng et al. Acoustic separation of circulating tumor cells. PNAS, Apr. 21, 2015, vol. 112, No. 16. p. 4970-4975.

HIGH THROUGHPUT ACOUSTIC PARTICLE SEPARATION METHODS AND DEVICES

STATEMENT REGARDING FEDERALLY SPONSORED RESEARCH & DEVELOPMENT

This application is a U.S. National Phase Application of PCT/US2017/022484, now WO/2017/160964, filed Mar. 15, 2017, which claims the benefit of priority to U.S. Provisional Application No. 62/308,547, filed Mar. 15, 2016, the contents of which are hereby expressly incorporated by reference in their entirety.

CROSS REFERENCE TO RELATED APPLICATIONS

This invention was made with government support under grants RR025713 and GM103448 and GM112398 awarded by the National Institutes of Health. The government has certain rights in the invention.

BACKGROUND OF THE DISCLOSURE

The present disclosure relates generally to devices and methods for particle focusing, entrapment, manipulation, and separation, including high throughput acoustic particle separation.

Efficient separation of particles and cells is essential to many biological and medical applications, particularly for diagnosis and prognosis of cancers and viral infections. Isolation of cells with a relatively low abundance (monocytes in whole blood) or extreme rarity (circulating tumor cells in blood or pathogenic bacteria in water samples) is a significant challenge. Due to the dimensional similarity of cells (~1-10 s of μm) and typical microchannels (~10 s to 100 s of μm), microfluidics is well-suited to isolation, enrichment, and analysis of cells and cell-like objects, exploiting minute differences in their inherent physical characteristics (size, shape, density, deformability, compressibility, electrical polarizability, magnetic susceptibility, and refractive index) to manipulate targeted cells of a larger population. For example, particles suspended in a liquid rapidly migrate to pressure minima (nodes)/maxima (antinodes) when subjected to a spatially varying acoustic field.

Acoustophoresis is continuous-flow particle separation in spatially varying acoustic fields. Attractive or repulsive acoustic radiation forces (ARFs) arise due to differences in the acoustic properties of suspended particles and surrounding medium (acoustic contrast, $\Phi$), as well as the particle size and shape. Because the magnitude and direction of these forces are functions of particle size and a material-dependent contrast factor, this phenomenon can be utilized to trap objects locally over an ultrasonic transducer, to concentrate them within a fluidic channel, and to align, sort or separate different types of objects. These attributes have proven beneficial in a number of biomedical and life sciences applications, from particle trapping to enhance bead-based bioanalytic assays to simple medium exchange to separation of lipid particles from blood during cardiopulmonary bypass surgery. Blood is particularly well-suited to acoustophoretic separation of its various components due to particle size restrictions (~1-20 μm for typical ultrasound frequencies in the low MHz range) and the relative gentleness of acoustophoresis, which has been shown to elicit minimal immediate or long-term changes in cell viability or proliferation.

The magnitude of the ARF is directly proportional to the acoustic contrast factor $\Phi$ $$\Phi = \frac{(5\tilde{\rho} - 2)}{(2\tilde{\rho} + 1)} - \tilde{\kappa} \text{ where } \tilde{\rho} = \rho_p/\rho_o \text{ and } \tilde{\kappa} = \kappa_p/\kappa_o.$$

The ratios of particle/media density and compressibility, $\tilde{\rho}=\rho_p/\rho_o$ and $\tilde{\kappa}=\kappa_p/\kappa_o$, respectively, prescribe the sign of $\Phi$, which dictates whether particles migrate to the nodes (positive contrast particles) or antinodes (negative contrast particles) of a pressure wave. Glass, polystyrene and poly (methyl methacrylate) (PMMA) beads, and biological cells in aqueous media are examples of positive contrast particles. Gas filled beads and silicone rubber (PDMS) have negative contrast.

Separation of blood components is a critical step for most blood-based diagnostic procedures. The need for simple, portable, and low cost point-of-care (POC) diagnostics has heightened interest in microfluidic approaches to blood separations including size exclusion, sedimentation, inertial forces, micro-filtration, and acoustic forces. Among these several techniques, acoustophoretic separation offers excellent biocompatibility and requires no modification of the cells or cell culture/separation media, enabling separation of blood components in their native states. Further, only acoustophoresis allows different blood cell types from the same sample to be isolated by dynamically adjusting the acoustic radiation force. Although these advantages have been demonstrated in controlled laboratory settings using representative samples (e.g., cultured cancer cells (CTCs) from white blood cells (WBCs)), separation of whole blood from patients has proven difficult due to insufficient throughput and poor long-term operational stability in existing devices based on two-dimensional (2D) separation channels.

In describing a pressure wave (or field), the orientation/direction of the wave is defined as the direction in which one moves from a maximum to a minimum to a maximum (etc.) in amplitude. In typical free-flow acoustophoresis, the wave is perpendicular to the flow direction. That is, in existing acoustophoretic systems, the nodes (or nodal planes) of the acoustic field are parallel to the direction of flow. For a parallel wave, separation occurs perpendicular to the field orientation (because nodal/antinodal planes are positioned perpendicular to the flow direction).

The disclosure provides for devices and methods for particle focusing, entrapment, manipulation, and particularly high throughput separation. A device for high throughput separation may include a channel or reservoir for receiving a fluid comprising an array of openings on at least one side of the channel or reservoir, a transducer or actuator for generating a pressure field not perpendicular to the flow of the fluid through the channel or reservoir, wherein at least one node and at least one antinode of the pressure field are within the reservoir, an acoustic coupling layer, and an isolation layer. A method of high throughput separation of a plurality of objects may include receiving a suspension of objects in a fluid into a channel or reservoir comprising perforated walls for fluid entry and/or exit in a flow direction, generating a pressure field between the walls of the channel or reservoir, wherein at least one node and at least one antinode of the pressure field are within the reservoir, separating the plurality of objects within the fluid, wherein at least a first object is retained within the reservoir and at least a second object is passed from the channel or reservoir through the array of openings. The objects may be selected from the group consisting of particles, cells, and microorganisms. The pressure field may be an acoustic field. The pressure field may be non-perpendicular, or in some embodiments parallel, to the bulk flow of fluid.

BRIEF DESCRIPTION OF THE INVENTION

One embodiment of the present disclosure describes a device comprising a reservoir for receiving a fluid in a flow direction and a transducer for generating a pressure field that is not perpendicular to the flow direction of the fluid through the reservoir.

Another embodiment of the present disclosure describes a method of high throughput separation of a plurality of objects. The method comprises receiving a fluid in a flow direction into a reservoir comprising an array of openings on at least one side of the channel or reservoir; generating a pressure field that is not perpendicular to the flow of the fluid through the reservoir, wherein at least one node and at least one antinode of the pressure field are within the reservoir; and separating the plurality of objects within the fluid, wherein at least a first object is retained within the reservoir and at least a second object is passed from the reservoir through the array of openings.

Yet another embodiment of the present disclosure describes a device for high throughput separation comprising a reservoir for receiving a fluid in a flow direction comprising an array of openings on at least one side of the channel or reservoir; at least one acoustic reflective wall located within the reservoir, wherein the wall is not parallel to the flow direction and wherein the wall is perforated to allow fluid flow through the wall in the flow direction; and a transducer configured to generate a pressure field that is not perpendicular to the flow direction of the fluid through the reservoir, wherein at least one node and at least one antinode of the pressure field are within the reservoir.

Additional embodiments, aspects, and features are set forth in part in the description that follows, and will become apparent to those skilled in the art upon examination of the specification or may be learned by the practice of the disclosed subject matter. A further understanding of the nature and advantages of the disclosure may be realized by reference to the remaining portions of the specification and the drawings, which form a part of this disclosure.

BRIEF DESCRIPTION OF THE DRAWINGS

The disclosure will be better understood, and features, aspects, and advantages other than those set forth above will become apparent when consideration is given to the following detailed description thereof. Such detailed description makes reference to the following drawings, wherein.

DETAILED DESCRIPTION OF THE DISCLOSURE

The disclosure may be understood by reference to the following detailed description, taken in conjunction with the drawings as described below. It is noted that, for purposes of illustrative clarity, certain elements in various drawings may not be drawn to scale.

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred methods and materials are described below.

Figure 1:
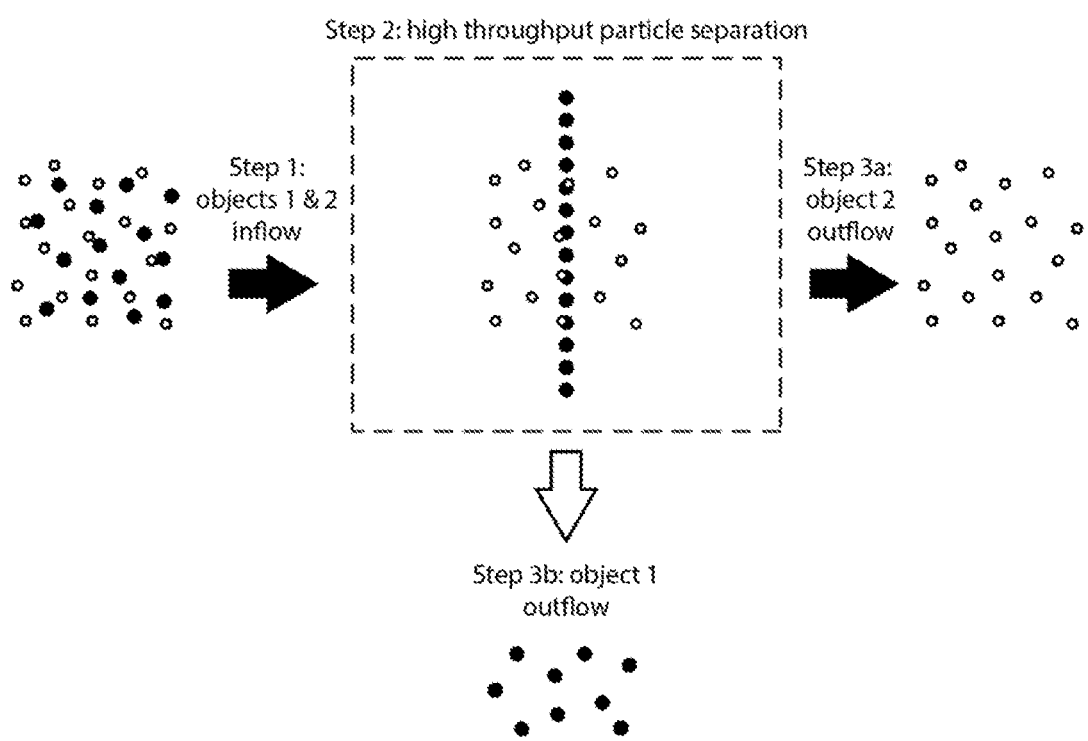
FIG. 1 depicts an exemplary embodiment of a multistep high-throughput separations method, in accordance with the present disclosure.
Figure 2:
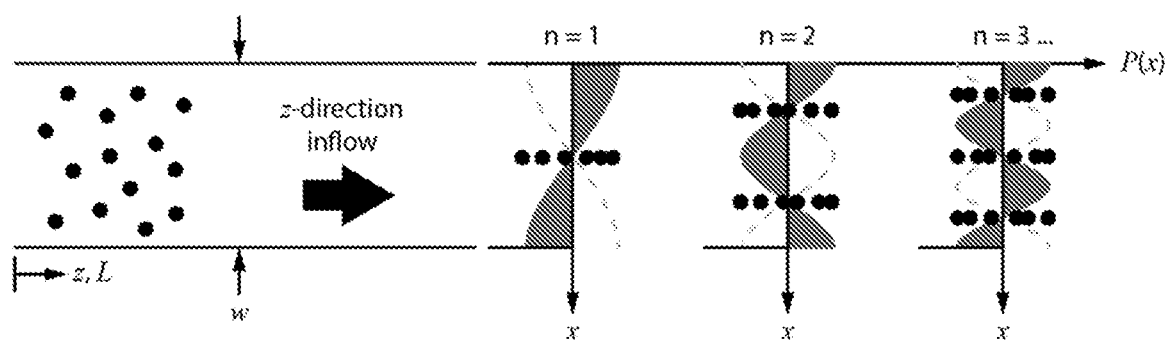
FIG. 2 depicts an exemplary embodiment of conventional microchannel acoustophoresis, in accordance with the present disclosure.
Figure 3:
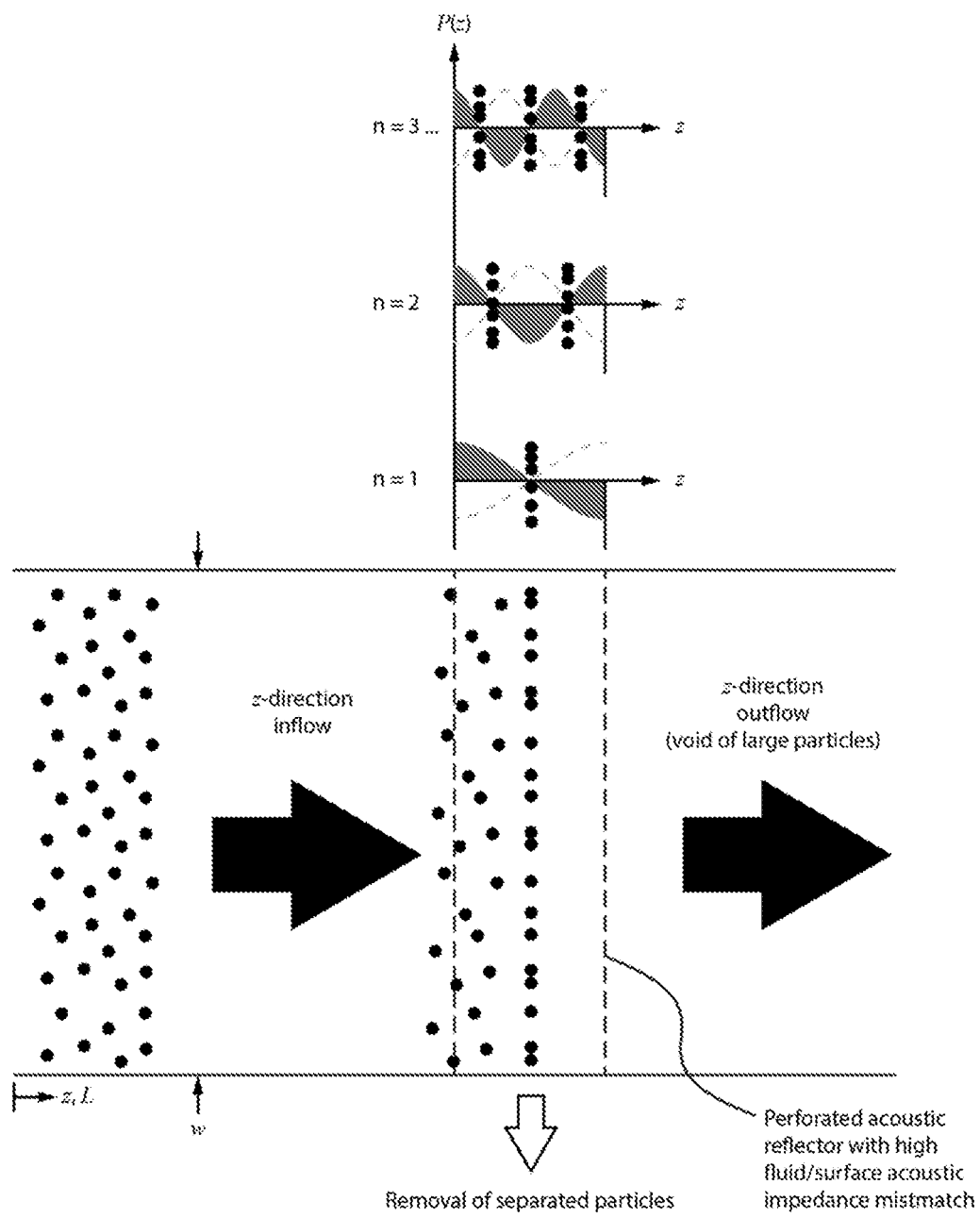
FIG. 3 depicts an exemplary embodiment of a system that can perform high throughput acoustophoresis, in accordance with the present disclosure.

Provided herein are high throughput acoustophoretic methods and devices for the focusing, retention and separation of particles and/or cells in continuous flow through the device. FIG. 1 illustrates the most general technology embodiment. Depending on the embodiment, the high throughput acoustophoretic device may have any geometry that performs continuous flow separation of particles/cells using a spatially varying acoustic field with nodal/antinodal planes perpendicular to the direction of flow. In some embodiments, the high throughput device may have an electrosonic actuation microarray (EAM)-like geometry and may focus cell-size particles. In existing acoustophoretic systems, the nodes of the acoustic field are oriented parallel to the direction of flow. The spatially varying acoustic field with nodal/antinodal planes may be non-parallel to the direction of flow in the present device, allow for retention of a particle or cell within the device, and allow for high throughput separation. In some embodiments, the nodal/antinodal planes may be perpendicular to the direction of flow.

Figure 7:
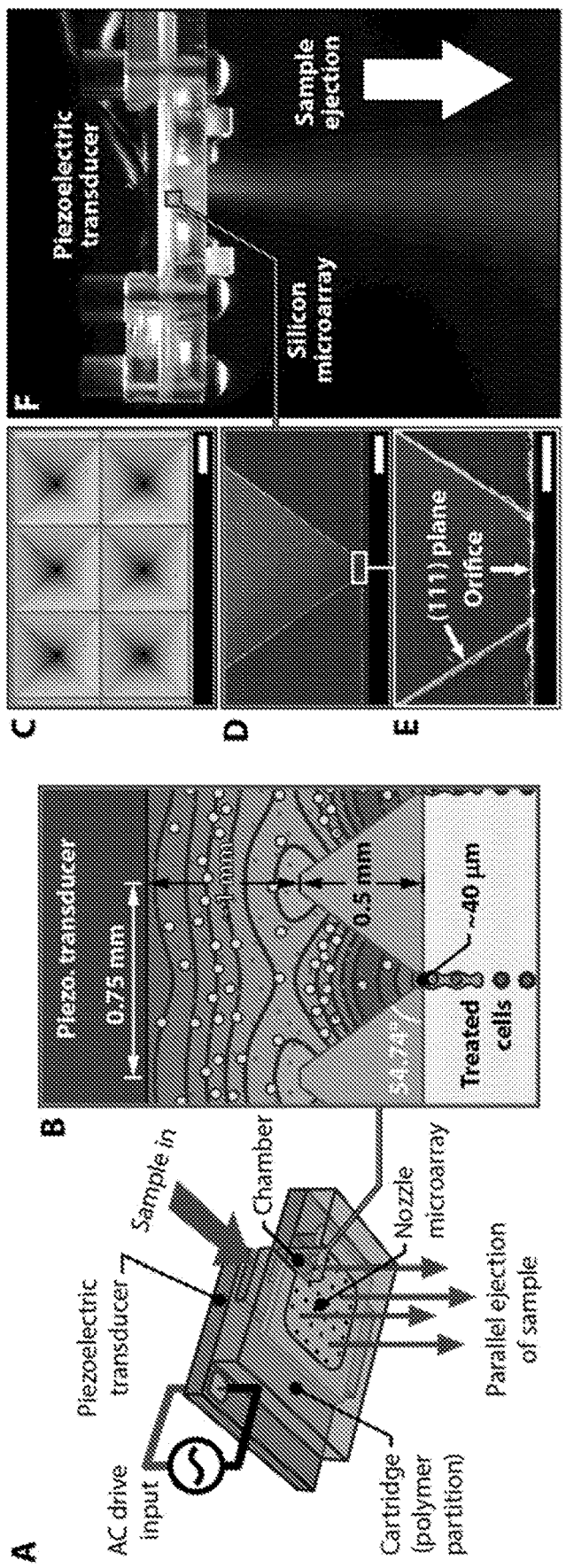
FIG. 7A depicts an exemplary embodiment of an Electrosonic Actuation Microarray (EAM), 3D schematic of device concept, in accordance with the present disclosure.
FIG. 7B depicts an exemplary embodiment of an Electrosonic Actuation Microarray (EAM), detail of a single nozzle illustrating resonant acoustic field focusing that drives sample ejection and mechanoporation of biological cells, in accordance with the present disclosure.
FIG. 7C depicts an exemplary embodiment of an Electrosonic Actuation Microarray (EAM), SEM image of fabricated silicon nozzle microarrays (scale bar is 300 µm), in accordance with the present disclosure.
FIG. 7D depicts an exemplary embodiment of an Electrosonic Actuation Microarray (EAM), SEM side view image of a fabricated silicon nozzle (scale bar is 100 µm), in accordance with the present disclosure.
FIG. 7E depicts an exemplary embodiment of an Electrosonic Actuation Microarray (EAM), SEM side view image of a fabricated silicon nozzle (scale bar is 25 µm), in accordance with the present disclosure.
FIG. 7F depicts an exemplary embodiment of an Electrosonic Actuation Microarray (EAM), sample ejection from an assembled prototype device, in accordance with the present disclosure.

The Electrosonic Actuation Microarray (EAM) device was originally conceived to impose an identical and carefully controlled electromechanical environment on individual cells of a larger population to promote cell membrane poration and DNA delivery into cells as they are ejected one-by-one through cell-sized orifices. FIG. 7 illustrates a basic technology embodiment. The EAM comprises a piezoelectric transducer for ultrasound wave generation, a reservoir containing sample mixture, and a planar array of acoustic horn structures for focused application of mechanical stimuli. When driven at particular resonant frequencies of the fluid-filled horn structures, focused acoustic waves establish a favorable pressure gradient at the nozzle tips driving fluid transport through cell-sized orifices (see FIGS. 7B and 7F). As a consequence, suspended cells are exposed to mechanical shear forces that induce temporary and reversible poration of the cell membrane. The mechanical microenvironment at the nozzle tips is imposed on each cell individually enabling high delivery efficacy for a broad range of cell types and cargo molecules.

Under certain operating conditions, the concentration of cells in the collected sample may be significantly lower than that of the sample loaded into the reservoir of the EAM. Cells become trapped in the standing acoustic pressure field that is used to drive ejection from the orifices of the microarray. Acoustic particle retention is detrimental to the cell treatment performance of the EAM. For this reason, various approaches to minimize particle trapping have been evaluated including frequency modulation (e.g., to switch between "focusing" and "dispersive" pressure fields), use of a back pressure to drive flow from the nozzles at a lower pressure field amplitude (e.g., to reduce the focusing force while maintaining flow from the nozzles), and use of sample additives to reduce the acoustic contrast between cells and cell media. Of these potential solutions, only modification of the media properties has appreciably improved the collection efficiency at certain operating conditions. Addition of ~10% v/v sucrose to increase the density of the media to that of the cells resulted in almost 100% collection. Unfortunately, at high sucrose concentrations, cells do not fully recover from treatment by the EAM.

In conventional microscale acoustofluidic particle manipulation, particles are manipulated by traveling or standing waves (in both cases, primary acoustic radiation force (ARF) drives particle motion) or acoustic streaming (acoustic waves generate motion in a fluid, which then "pulls" particles along due to drag). The high throughput acoustophoresis device provided herein uses standing wave manipulation of particles using ARF. Acoustic radiation force (for spherical particles in standing plane waves) is directly proportional to the acoustic contrast factor (which is a function of the density and compressibility ratios of the particles and fluid). ARF is also proportional to the particle volume (or radius to the third power, $a^3$) and the acoustic energy density, $E_{ac}$, which is a function of the acoustic pressure amplitude (larger for larger pressure amplitude), and ARF is inversely (directly) proportional to the wavelength (frequency) of the plane wave. For particles of different sizes and properties, the differences in the magnitude and direction of the ARF are due to the different particle sizes, densities, and compressibilities. For a given particle (fixed size and properties), the magnitude of the ARF (and thus the driving and holding force for acoustic particle separation) can be increased by increasing the frequency of operation (subject to limitations on available frequencies of operation) and by increasing the amplitude of the pressure field, for example, by modifying material properties of the structure to increase the acoustic impedance mismatch between the microchannel walls and the fluid or changing the geometry to enhance constructive interference of acoustic waves within the fluid. In some embodiments, the pyramidal nozzle array of the EAM may focus acoustic waves to generate a higher pressure amplitude for driving ejection of fluid. Therefore, geometry may be used to dictate frequencies of operation or to enhance the separation through geometric focusing of acoustic waves (e.g., use of various acoustic horn shapes).

Any multiple of half the wavelength $\lambda$ of a standing wave can be equated to the distance, d (i.e., (2d)/1, (2d)/2, (2d)/3 . . . ), between two surfaces (acoustic reflectors, or pseudo surfaces/acoustic reflectors). The denominator of the expression for wavelength as a function of distance is the mode, n, of the resonating geometry. The actuation frequencies, f, available to generate a standing acoustic wave between the two surfaces are then dictated by these wavelengths and the speed of sound, c, within the fluid as $f=c/\lambda=nc/(2d)$.

Typical separations are performed in water or water-like fluids, or blood and blood-like fluids with c~1500 m/s. The threshold frequency for microfluidic separation of a 10 μm particle (representative of cells and cell-like objects) in water is about 1 MHz. Below 1 MHz, the ARF may be not large enough to overcome viscous drag (which acts against ARF), and particles move only very slowly toward nodes/antinodes of the acoustic field. For smaller particles, higher frequency pressure fields are required to effect good focusing; however, high frequency (short wavelength) acoustic waves are subject to significant attenuation over short distances. For example, the larger the number of wavelengths of an acoustic field present between the geometric boundaries (walls) of a microchannel, the greater the attenuation of the amplitude of the pressure wave, which leads to a decrease in the ARF. For this reason, the number of wavelengths (mode number) of the acoustic field is typically limited to less than about 3 wavelengths. For cell-like objects suspended in water-like fluids, separations are typically carried out in the frequency range of about 1 MHz to about 20 MHz, which corresponds to a first mode half-wavelength of about 0.75-0.04 mm, or if limited to n<6, d must be less than approximately 0.25 to 4.5 mm. Separation of larger particles or particles with larger acoustic contrast may be performed with larger inter-reflector distances at lower frequencies. However, separation may be less effective for distances of above 10 mm in width or below 100 kHz for any particles of interest. The minimum distance between reflectors is based on attenuation in the fluid, but also on the size of the particles to be separated. In general, the wavelength of the acoustic field should be "large" (>about 5-10 times the diameter of a particle, a) compared to the size of the particles, so use of inter-reflector distances of less than half of 10 a or 50 μm for 10 μm diameter particles may be less effective.

Conventional separations are performed in single or parallel arrays of two-dimensional microchannels (see FIG. 2). Uniformly distributed particles enter a focusing/separation zone where a standing acoustic field is oriented non-parallel (e.g., perpendicular) to the flow (i.e., in the x-direction) between walls of the microchannel. In general, any mode of the acoustic field can be used subject to the limitations described above. As particles flow along the acoustically active zone, they gradually migrate to nodes/antinodes (depending on positive/negative acoustic contrast of the particles) of the standing acoustic wave. The time required to adequately focus a given particle is dependent upon the magnitude of the ARF, and the particle location relative to the node/antinode of the field when it enters the acoustically active zone. The residence time of the particle is equal to the length of the channel divided by the flow velocity. If the residence time is not greater than the time required to adequately focus a given particle, the particle will not be separated from the bulk flow. For this reason, if the ARF is not large enough, due to low frequency operation, low pressure wave amplitude, small particle diameter, or small acoustic contrast, the channel is not long enough, or the flow rate is too high, a given microfluidic device will not be able to adequately separate a heterogeneous particle suspension. Thus, for particles with smaller differences in acoustic contrast and size, a given separations device may need a lower flow rate (limiting throughput) or an unreasonably long channel.

High throughput separations can be achieved by orienting the acoustic field parallel to the direction of flow (see FIGS. 3-6 and 14) or at least not perpendicular to the direction of flow. In this way, all suspended particles must flow through the nodes/antinodes of the acoustic field during a spatial distance on the order of that of the wavelength of the acoustic field. The acoustic field is maintained between perforated acoustic reflectors made of materials with substantially higher acoustic impedance as compared to the fluid. Perforations in reflector walls allow suspended particles to flow through while not significantly affecting the acoustic field structure or strength. The strength of the ARF during transit through the acoustically active zone can be increased by decreasing the distance between reflectors (i.e., by allowing operation at higher frequencies). Indeed, a device may contain a series of reflector pairs of different spacing to allow separation of a heterogeneous suspension into its various constituent particles (e.g., for whole blood, large white blood cells may be separated by widely spaced reflectors and red blood cells may be separated by closely spaced reflectors). Because the acoustic field is oriented parallel (or at least non-perpendicular) to the direction of flow, the width, w, of the microchannel (and therefore its cross-sectional area, $A_c$, can be increased without affecting the frequency of operation. This allows for increased throughput at a given flow velocity, v (flow rate, $Q=v\,A_c$) or for increased flow rate since pressure drop at a given flow rate will be less (assuming that ARF is still strong enough to overcome drag and to focus particles). If needed, removal of separated particles may be performed in sequential steps where separation is followed by flow in an orthogonal direction.

The high throughput acoustophoretic device may include an actuator and a channel or reservoir. In some embodiments, the channel or reservoir may have high acoustic impedance relative to the fluid and may be suitable for geometric arrangement for the development/maintenance of a standing pressure field suitable for trapping objects. The actuator may generate a standing pressure field. In some embodiments, the actuator may generate an ultrasonic wave. The actuator may include, but is not limited to, a piezoelectric actuator, a capacitive actuator, or an array of interdigitated electrodes. The device may further include acoustic coupling layer and an isolation layer. In some embodiments, the acoustic coupling layer may be an aluminum coupling layer. In some embodiments, the isolation layer may be a silicon isolation layer. In some embodiments, the high throughput acoustophoretic device may be an EAM device.

Figure 4:
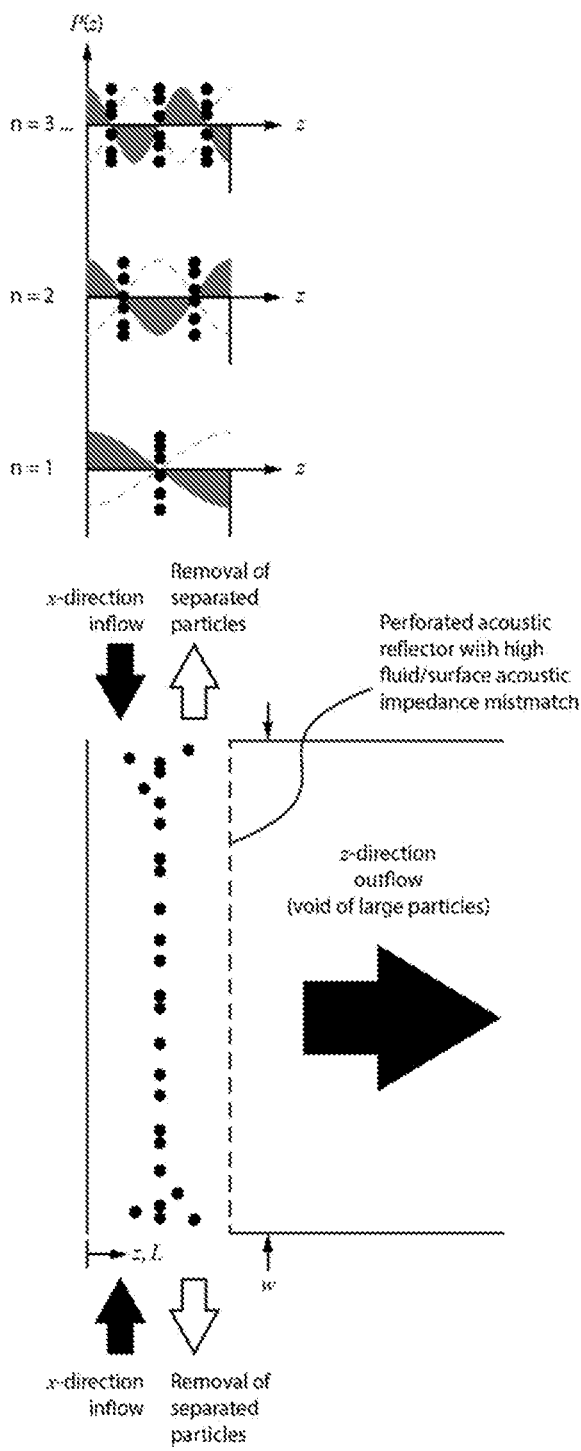
FIG. 4 depicts another exemplary embodiment of a system that can perform high throughput acoustophoresis, in accordance with the present disclosure.

Depending on the embodiment, the reservoir may include an array of openings on a side opposite to the actuator. In some embodiments, nodal/antinodal planes may be established between solid and/or perforated surfaces in the reservoir. For example, the piezoelectric actuator surface may be the solid surface and a nozzle array may be the perforated surface. The ultrasound transducer may be a piezoelectric transducer in some embodiments. High-throughput separations may also be performed in a reflector arrangement where one of the perforated reflectors may be replaced by a solid reflector (see FIGS. 4 and 6). A heterogeneous particle suspension may enter in the x-direction at the top and bottom of the acoustically active zone and exit to the right after particle separation and focusing in the z-direction. Effective separation in this geometry may be subject to the same limitations described herein above. One embodiment of this arrangement may be an ultrasonic droplet generator (see FIGS. 7 and 10).

Flow may be driven by any source of pressure differential including, but not limited to an acoustic pressure source such as an ultrasound transducer, a pressure pump, a gas cylinder, a compressor, a vacuum pump, a syringe (manual or syringe pump), a peristaltic pump, a pipette, a piston, a capillary actor, any mechanical device, and gravity. It is not necessary that the fluid motion is driven by acoustic waves. In some embodiments, fluid may be pumped through the orifices of the nozzle plate using pressure; however, the reflectors (1 solid and 1 perforated pseudo wall) need to meet the requirements provided herein. In some embodiments, the device may include 2 perforated reflectors, and may not have limitations on flow rate.

In general, the material of the acoustic coupling layer and any isolation layers should have a low ultrasonic acoustic attenuation. The coupling layer and isolation layers may be made of materials such as, but not limited to, single crystal silicon (e.g., oriented in the (100), (010), or (001) direction), metals (e.g., aluminum, copper, stainless steel and/or brass), plastics, silicon oxide, quartz, glass, silicon nitride, and combinations thereof.

In general, the material that the channel structure is made of may have substantially higher acoustic impedance as compared to the fluid. The channel may be made of materials such as, but not limited to, single crystal silicon (e.g., oriented in the (100), (010), or (001) direction), metals (e.g., aluminum, copper, stainless steel and/or brass), plastics, silicon oxide, quartz, glass, silicon nitride, and combinations thereof.

In some embodiments, an actuator may produce a resonant ultrasonic wave within the reservoir and fluid. The resonant ultrasonic wave couples to and transmits through the liquid and is focused by ejector structures. The high-pressure gradient accelerates fluid out of the ejector structure to produce droplets. The droplets are produced due to break up of a continuous jet or discretely in a drop-on-demand manner. The frequency at which the droplets are formed is a function of the drive cycle applied to the actuators as well as the fluid, reservoir and ejector structure, and the ejector nozzle.

An alternating voltage is applied to the actuator to cause the actuator to produce the resonant ultrasonic wave. The actuator can operate at about 100 kHz to 100 MHz, 500 kHz to 15 MHz, and 800 kHz to 5 MHz. A direct current (DC) bias voltage can also be applied to the actuator in addition to the alternating voltage. In embodiments where the actuator is piezoelectric, this bias voltage can be used to prevent depolarization of the actuator and can also generate an optimum ambient pressure in the reservoir. In embodiments where the actuator is electrostatic, the bias voltage is needed for efficient and linear operation of the actuator. Operation of the actuator is optimized within these frequency ranges in order to match the cavity resonances, and depends on the dimensions of and the materials used for fabrication of the reservoirs and the array structure as well the acoustic properties of the operating fluid.

The dimensions of the coupling and isolation layers, if present, are chosen such that the thicknesses of the coupling and isolation layers are approximately multiples of half the wavelengths of longitudinal waves in the coupling and isolation layers at the frequency of operation. Therefore for typical coupling materials like quartz, aluminum and silicon, the dimensions of the coupling and isolation layers are from 100 micrometers to 50 centimeters in width, 10 micrometers to 50 centimeters in thickness, and 100 micrometers to 50 centimeters in length. In addition, the dimensions of the coupling and isolation layers are from 100 micrometers to 2 centimeters in width, 10 micrometers to 10 millimeters in thickness, and 100 micrometers to 2 centimeters in length. Further, the dimensions of the coupling and isolation layers are from 100 micrometers to 1 centimeters in width, 10 micrometers to 2 millimeters in thickness, and 100 micrometers to 1 centimeter in length.

The dimensions of the actuator may depend on the type of actuator used. In some embodiments, where the actuator is a piezoelectric actuator, the thickness of the actuator is determined, at least in part, by the frequency of operation and the type of the piezoelectric material. The thickness of the piezoelectric actuator is chosen such that the thickness of the actuator is about half the wavelength of longitudinal waves in the piezoelectric material at the frequency of operation. Therefore, in the case of a piezoelectric actuator, the dimensions of the actuator are from 100 micrometers to 4 centimeters in width, 10 micrometers to 1 centimeter in thickness, and 100 micrometers to 4 centimeters in length. In addition, the dimensions of the actuator are from 100 micrometers to 2 centimeters in width, 10 micrometers to 5 millimeters in thickness, and 100 micrometers to 2 centimeters in length. Further, the dimensions of the actuator are from 100 micrometers to 1 centimeters in width, 10 micrometers to 2 millimeters in thickness, and 100 micrometers to 1 centimeter in length.

The high throughput acoustophoresis device may be used for isolation of particles, microorganisms, and/or cells including, but not limited to immune cells, circulating tumor cells (CTCs), bacterial cells, macromolecules, nanoparticles, viruses, microparticles (polymeric, metallic, etc.), or any mammalian or non-mammalian cell. In some embodiments, the high throughput acoustophoretic device may isolate cells with relatively low abundance from whole blood or other bodily fluids. The standing pressure field formed in the sample reservoir at particular resonant frequencies is also conducive to separation and isolation of cell-sized (~1-50 µm) and sub-cellular (<1 µm) particles. In some embodiments, the resonant frequency may be 0.1 to 100 MHz. Stratification of nodal (zero pressure) and antinodal (maximum pressure amplitude) planes perpendicular, or at least not parallel, to the direction of bulk flow (i.e., the direction of sample ejection from the orifices of the microarray) offers a means of preferentially focusing (and thus retaining) cells of a particular size, shape, density or compressibility from a larger cell population.

Figure 10:
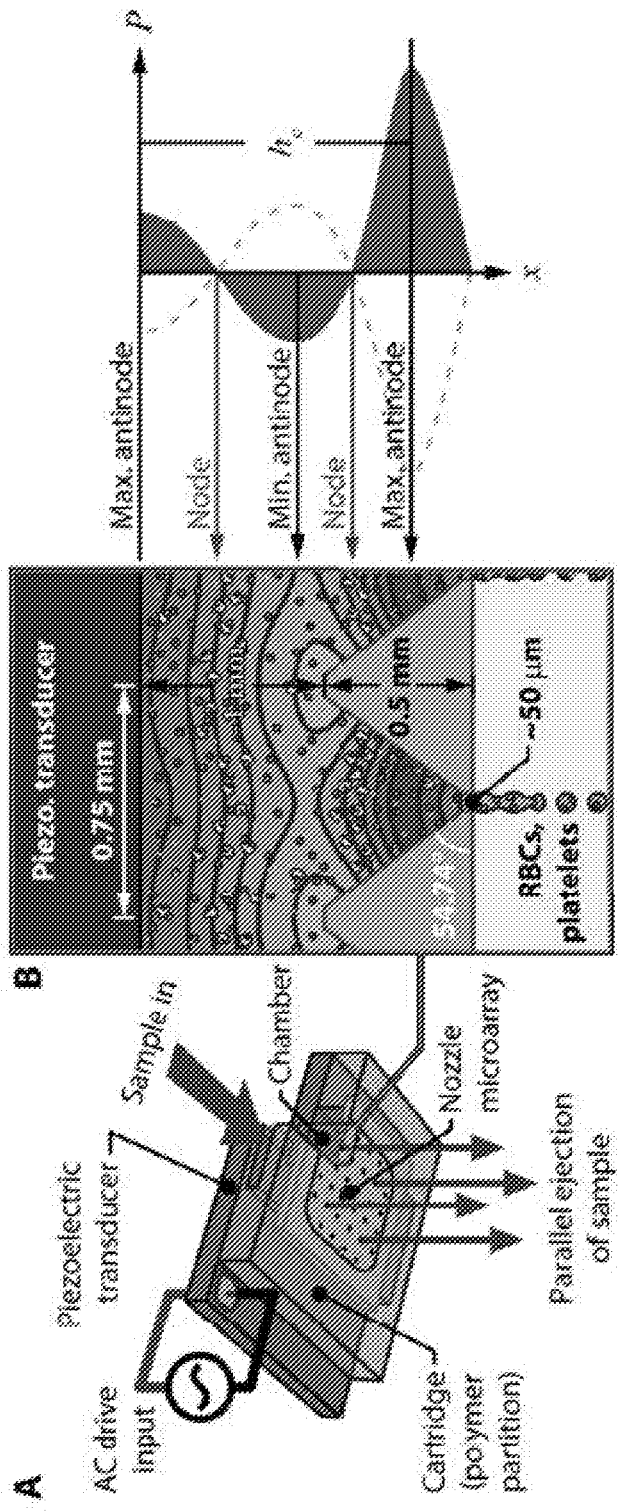
FIG. 10A depicts an exemplary embodiment of a conceptual high-throughput acoustic particle separation method/device, in accordance with the present disclosure.
FIG. 10B depicts an exemplary embodiment of a high-throughput acoustic particle separation method/device detailing separation of larger cells from red blood cells and platelets in a spatially varying acoustic field oriented perpendicular to the direction of bulk flow, in accordance with the present disclosure.

An embodiment of a high-throughput acoustic particle separation method/device is shown in FIG. 10. In this embodiment, there is an array of pyramidal nozzles from which a sample is ejected. FIG. 10 shows a plot of the pressure field within the chamber showing the two nodal planes where cells will focus. One antinode is located at the piezoelectric surface, and another antinode is located in the "middle" of the chamber. The final antinode is the pressure field focal point in the pyramidal nozzles, which is what drives ejection. That focal point dictates the "effective" height of the chamber. The distance between the piezoelectric surface and the pressure field focal point defines the dimension over which an acoustic wave is "standing". For example, for FIG. 10 there are 2 half-wavelengths of the field located between those two points. That represents the second half-wavelength resonance for the device. There are two nodes for focusing at this frequency. If the device were driven at a lower resonant mode, there would only be two antinodes and a single nodal plane for particle focusing.

Figure 11:
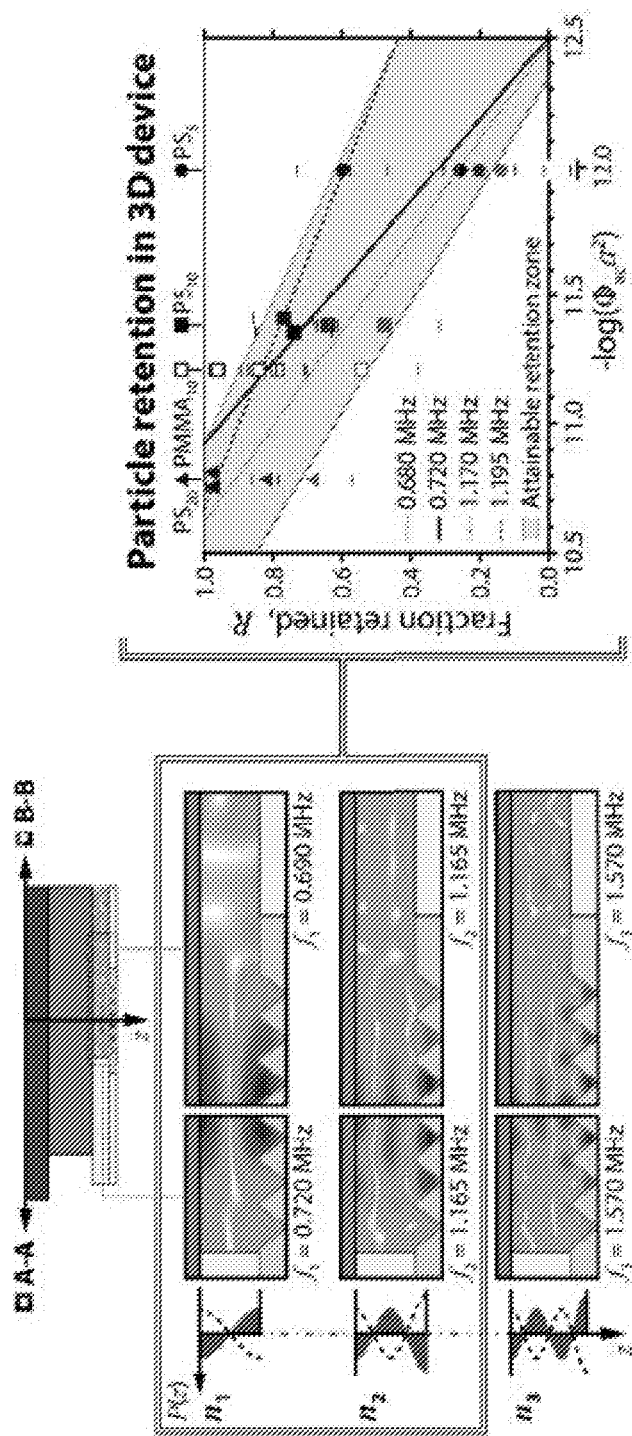
FIG. 11 depicts an exemplary embodiment of 3D Electronsonic Actuation Microarray (EAM) particle focusing modes and a plot of particles retained (y-axis) vs. acoustic focusing factor (x-axis) in accordance with the present disclosure. Nodes are shown as lighter (white) and antinodes are shown as darker (black).

FIG. 11 demonstrates preferential separation of a population of beads (5, 10, and 20 micron diameter) using a device similar to the one depicted in FIG. 10. FIG. 11 shows a plot of particles retained (y-axis) vs. acoustic focusing factor (some function of the acoustic contrast phi (which is a function of density and compressibility ratios of particles to fluid) and particle size (radius, a, squared)) for PS (polystyrene) and PMMA (poly(methyl methacrylate)) beads of various sizes. The PS and PMMA have different acoustic contrast due to their different material properties so a higher fraction of 10 micron PMMA particles is retained than the same size PS. The difference in retention of the three PS sizes may be purely a function of size. Various frequencies used for separation play a role in observed values. Spraying efficiency may vary at different frequencies. Accordingly, differences in behavior may be due to potential differences in acoustic behavior and definite differences in flow and drag on the particles. Nodes are shown as lighter (white) and antinodes are shown as darker (black).

Figure 5:
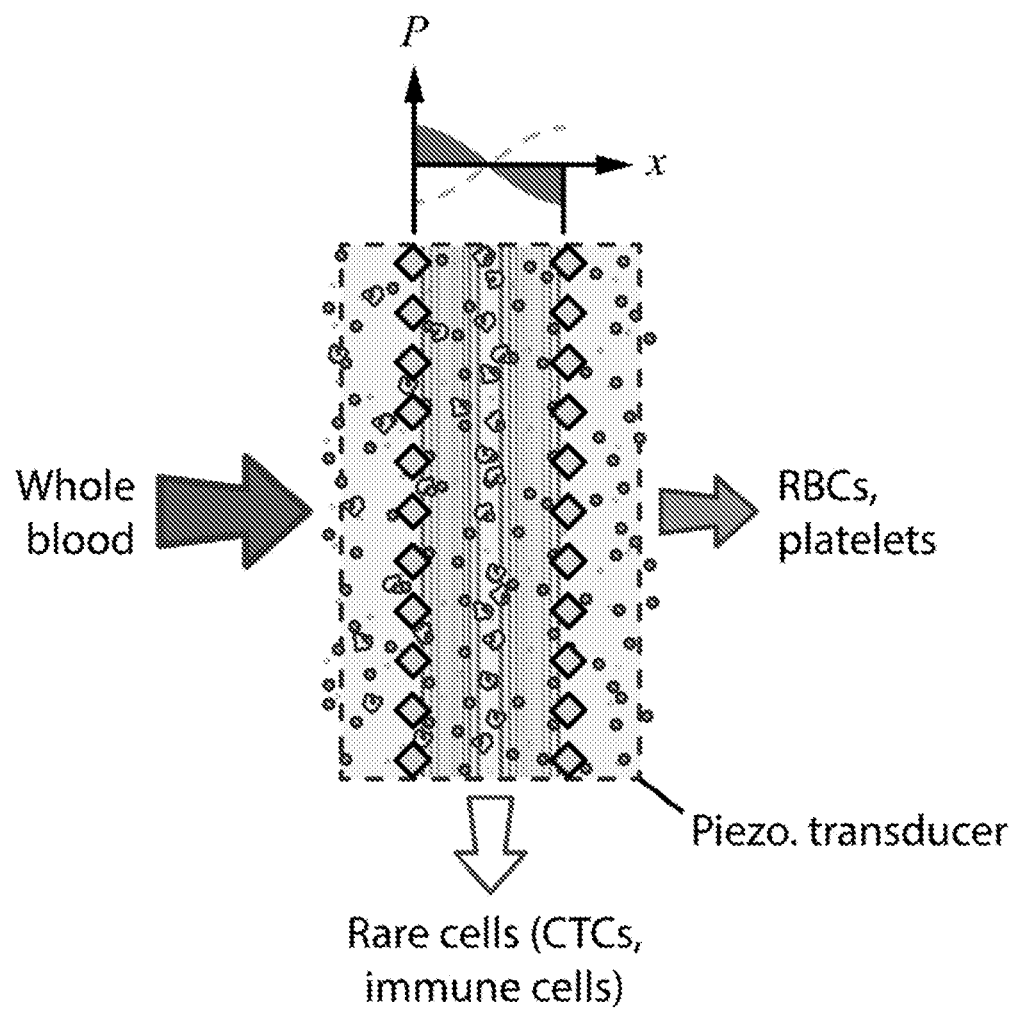
FIG. 5 depicts an exemplary embodiment of particle/cell focusing between two perforated walls where the overall flow is to the right (horizontal), but the field sets up nodal/antinodal lines (planes) in the vertical direction, in accordance with the present disclosure.
Figure 6:
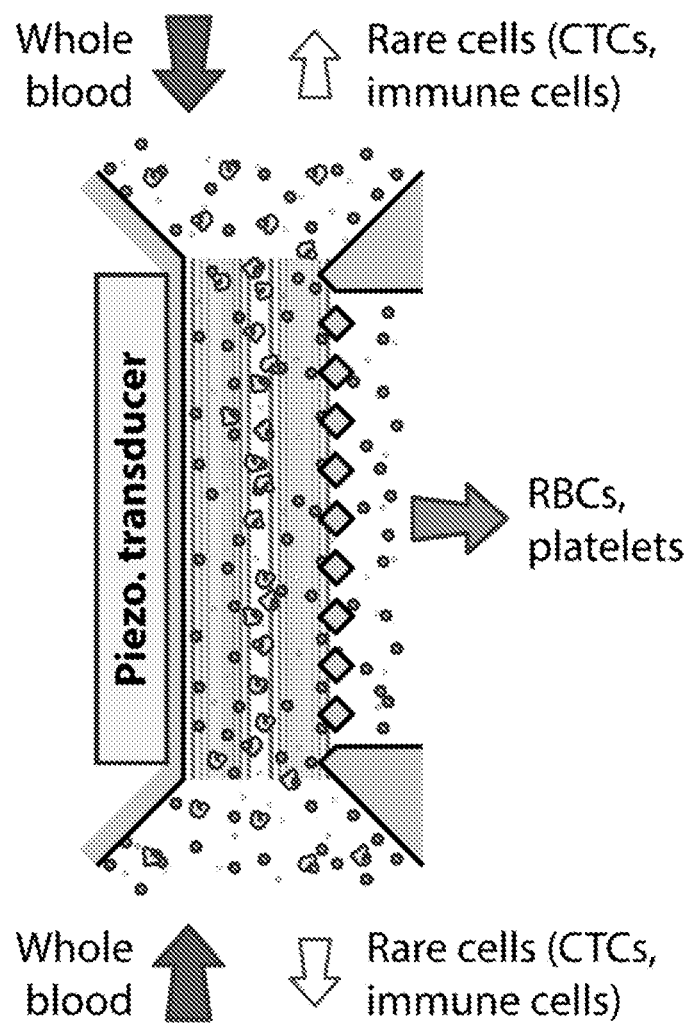
FIG. 6 depicts an exemplary embodiment of particle/cell focusing between one solid and one perforated wall where overall flow enters at the top and bottom and flows to the right (horizontal), but the field sets up nodal/antinodal lines (planes in the vertical direction), in accordance with the present disclosure.

FIGS. 5 and 6 illustrate particle/cell focusing between one perforated wall and one solid or perforated wall where overall flow is to the right (horizontal), but the field establishes nodal lines (planes) in the vertical direction. In some embodiments, there may be a single half-wavelength acoustic field "standing" between the geometric features so there is only one location where particles focus. This may be seen in FIGS. 5 and 6 as the single nodal line down the vertical center.

The high throughput acoustophoresis device may be used for isolation of rare cells from whole blood. Under an operating frequency of about 1 MHz, the particle size threshold for effective separation is ~10 µm (diameter) as the primary acoustic radiation force scales with the cube of the particle radius. Particles of smaller diameter (e.g., red blood cells (RBCs) and platelets) may be unaffected by the acoustic field, passing unimpeded through the sample reservoir and exiting from the nozzle orifices. In some embodiments, there may be preferential recovery of polystyrene beads with a diameter of about 5 µm (~100%) versus about 10 µm (<40%) during EAM ejection of a heterogeneous bead mixture. Isolation of specific targeted immune cells from a white blood cell population, where size differentials are less pronounced, may require characterization and optimization of EAM operating parameters. In some embodiments, separating particles with similar acoustic contrast may require sequential separation in the high throughput acoustophoresis device. Due to the inherent scalability of the planar microarray format, the three-dimensional (3D) high throughput acoustophoresis device addresses throughput limitations of traditional 2D microchannel acoustophoresis devices, not only enabling use of acoustic separations in a diagnostic tool, but potentially enabling therapeutic applications where high-throughput separation is essential.

Having described several embodiments, it will be recognized by those skilled in the art that various modifications, alternative constructions, and equivalents may be used without departing from the spirit of the invention. Additionally, a number of well-known processes and elements have not been described in order to avoid unnecessarily obscuring the present invention. Accordingly, the above description should not be taken as limiting the scope of the invention.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

EXAMPLE 1

Preliminary investigations were conducted of particle focusing in EAM-like geometries using a simplified 2D model and microfluidic chips that allowed visualization of particle migration under the action of an applied acoustic field. The acoustic simulation package of the commercial software ANSYS was used to predict how geometric parameters and material properties affect focusing performance.

Figure 8:
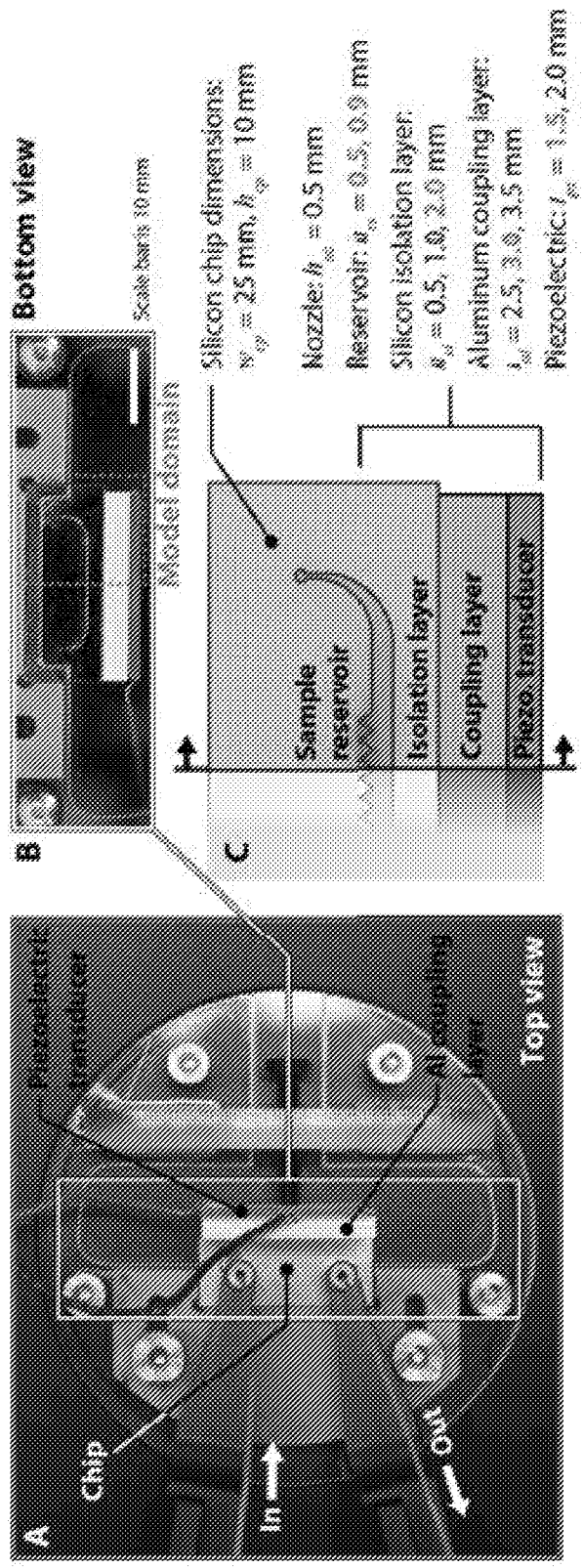
FIG. 8A depicts an exemplary embodiment of investigating acoustic particle focusing in 2D reservoirs that are representative of 3D Electronsonic Actuation Microarray (EAM) geometry, top view of the experimental setup used to visualize particle migration under the action of an applied acoustic field, in accordance with the present disclosure.
FIG. 8B depicts an exemplary embodiment of investigating acoustic particle focusing in 2D reservoirs that are representative of 3D Electronsonic Actuation Microarray (EAM) geometry, bottom view of the experimental setup used to visualize particle migration under the action of an applied acoustic field, in accordance with the present disclosure.
FIG. 8C depicts an exemplary embodiment of investigating acoustic particle focusing in 2D reservoirs that are representative of 3D Electronsonic Actuation Microarray (EAM) geometry, finite element analysis (FEA) domain used to model the acoustic response of the 2D assembly, in accordance with the present disclosure.

Single inlet, single outlet reservoirs designed to represent cross-sections of an injection-molded EAM cartridge were micro-machined into silicon and bonded to glass providing visual access to the "ejection" chamber (see experimental setup, FIGS. 8A and 8B). Nozzle tips were left closed to facilitate filling and testing of the device. While the acoustic response of a sealed cavity differs slightly from that of a reservoir with open orifices, these differences were not expected to significantly alter conclusions related to particle focusing behavior. The ANSYS simulation domain is shown in FIG. 8C. The listed component dimensions represent combinations of piezoelectric transducer thickness $t_{pz}$ (1.5 and 2.0 mm), aluminum coupling layer thickness $t_{al}$ (2.5, 3.0 and 3.5 mm), silicon isolation layer height $h_{si}$ (0.5, 1.0 and 2.0 mm), and reservoir height from the edge of the isolation layer to the nozzle base $h_{rs}$ (500 and 900 μm), which were available for experimental evaluation; however, the model is not limited to these component dimensions.

Figure 9:
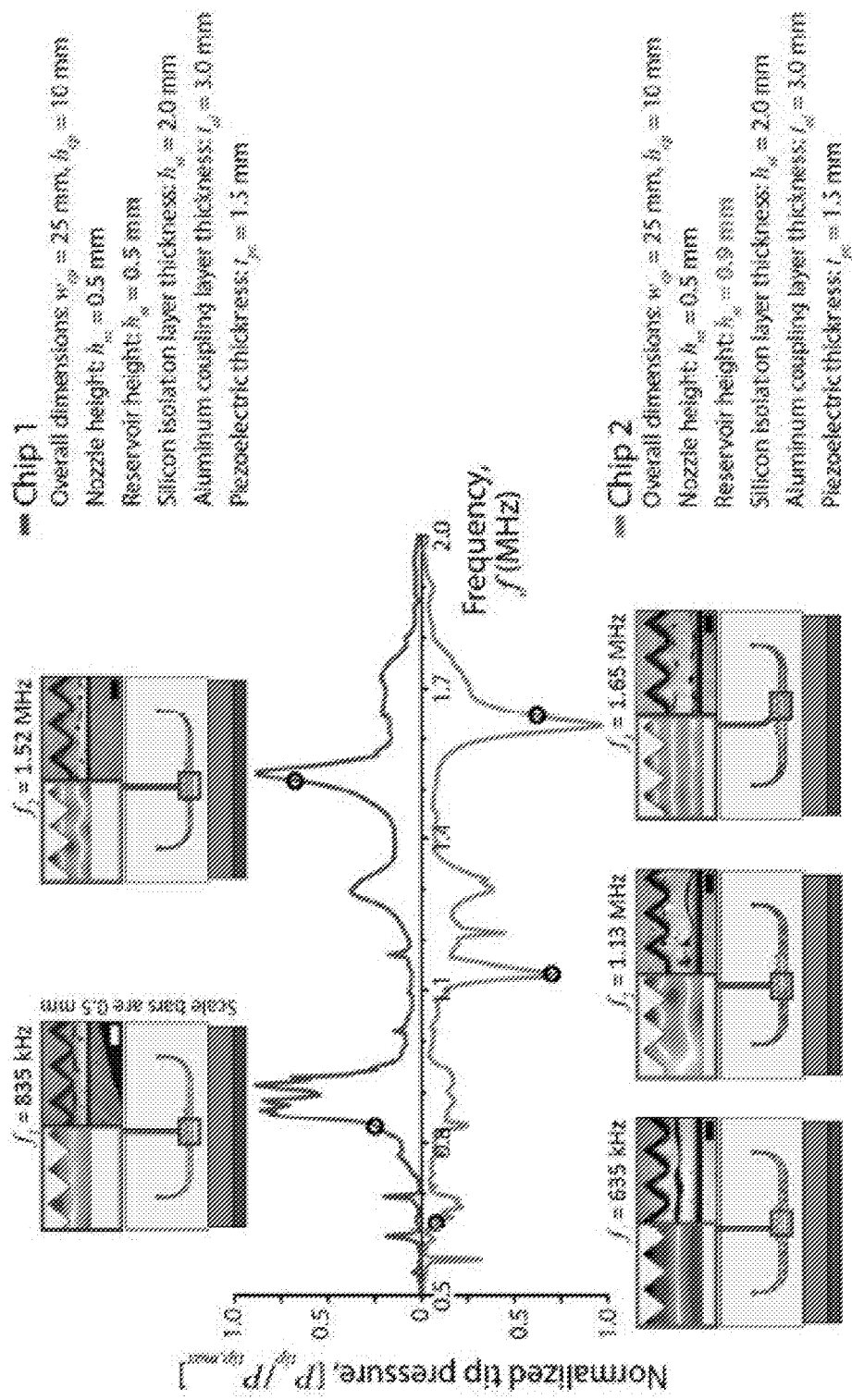
FIG. 9 depicts an exemplary embodiment of particle focusing in 2D reservoirs: tip pressure as a function of frequency is plotted for two different chip geometries, 500 µm reservoir height (Chip 1, top) and 900 µm reservoir height (Chip 2, bottom), in accordance with the present disclosure. Nodes are shown as lighter (white) and antinodes are shown as darker (black). Comparisons of predicted and observed terminal particle distributions are shown at resonant frequencies corresponding to ejection from the 3D Electronsonic Actuation Microarray (EAM).

The ANSYS model was used to predict focusing behavior for thirty six cases covering the combinations of geometric parameters listed in FIG. 8C. Chips with two different reservoir heights ($h_{rs}$=0.5 and 0.9 mm) were loaded with suspensions of 10 μm diameter polystyrene beads (density, τ=1.06 g cm$^{-3}$) and driven over a range of operating frequencies from 0.5 to 2.0 MHz. For conditions exhibiting intense particle activity, images were recorded after providing sufficient time to achieve a steady-state (terminal) particle distribution. While predictions were consistent with our existing understanding of EAM operation, the model demonstrated a remarkable ability to capture all details of the final particle distributions within different reservoir geometries. As expected, particles focused at the zero pressure nodes of the standing acoustic field when driven at frequencies corresponding to half-wave resonances of the fluid-filled reservoirs (see FIG. 9). The top line in FIG. 9 is a plot of normalized tip pressure as a function of frequency for Chip 1, a 0.5 mm reservoir; the bottom line is a plot of normalized tip pressure as a function of frequency for Chip 2, a 0.9 mm reservoir. Comparisons of predicted (ANSYS FEA) and observed terminal particle distributions at resonant frequencies corresponding to ejection from the 3D EAM (and falling within the 0.5 to 2.0 MHz frequency window) are also shown. The upper row of FIG. 9 shows the first two modes of a 0.5 mm reservoir, and the lower row the first three modes of a 0.9 mm reservoir. These results demonstrate the power of a combined modeling and visualization approach to studying the acoustophoretic separations process.

EXAMPLE 2

Figure 12:
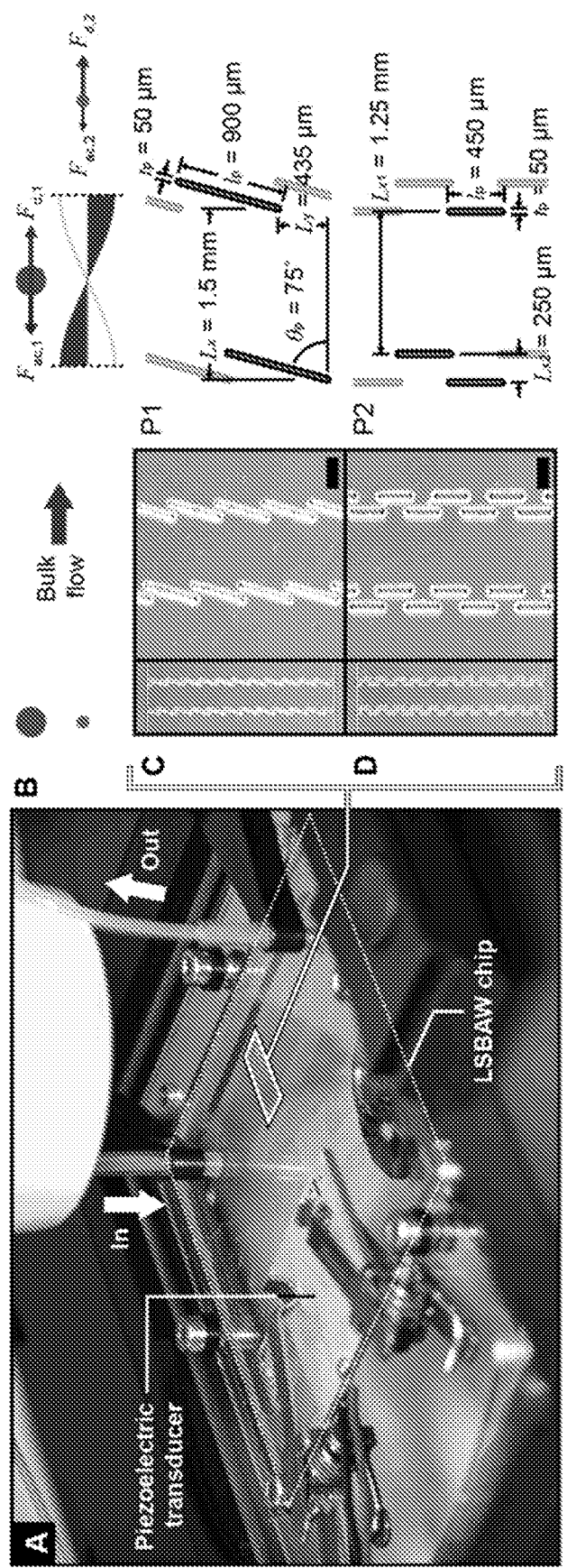
FIG. 12A depicts an exemplary embodiment of investigating acoustic particle focusing in 2D flow-through Longitudinal Standing Bulk Acoustic Wave (LSBAW) enrichment channels in accordance with the present disclosure.
FIG. 12B depicts an exemplary embodiment of a concept for high-throughput particle separation in a Longitudinal Standing Bulk Acoustic Wave (LSBAW) enrichment channel in accordance with the present disclosure.
FIG. 12C depicts an exemplary embodiment of parallel arrays of slanted (angle of inclination, $\theta p=75°$) pillars in the enrichment structure of a Longitudinal Standing Bulk Acoustic Wave (LSBAW) enrichment channel in accordance with the present disclosure.
FIG. 12D depicts an exemplary embodiment of parallel arrays of lamellar pillars in the enrichment structure of a Longitudinal Standing Bulk Acoustic Wave (LSBAW) enrichment channel in accordance with the present disclosure.

Separation of heterogeneous particle mixtures was demonstrated using suspensions of polystyrene beads (5 μm and 20 μm diameter at 5×105 and 2×106 per ml DI water, respectively; density 1.06 g cm$^{-3}$; Phosphorex) and hollow glass spheres (10 μm nominal diameter; Dantec Dynamics) decorated with fluorescent polyclonal secondary antibodies (rabbit anti-goat IgG Alexa Fluor 488; Abcam), which were synthesized in house. Separations microchannels with two different enrichment structures were etched into 1.5 mm thick soda lime/chromium blanks to a depth of ~60 μm using 49% (w/w) HF:69% (w/w) HNO3:DI water at a ratio of 2:1:6 (see FIGS. 12C,D). A second blank was bonded to the channel layer via calcium-assisted glass-glass bonding to seal the separations channel. Device actuation was achieved using a 24 mm×28 mm×1.5 mm thick PZT-8 piezoelectric transducer (P880, American Piezoelectric) clamped to the top side of the glass separations chip as shown in FIG. 12A. FIG. 12B indicates a bulk flow direction and separation of large from small particles at the first half-wave resonance of the structures shown below in FIGS. 12C and 12D.

Figure 13:
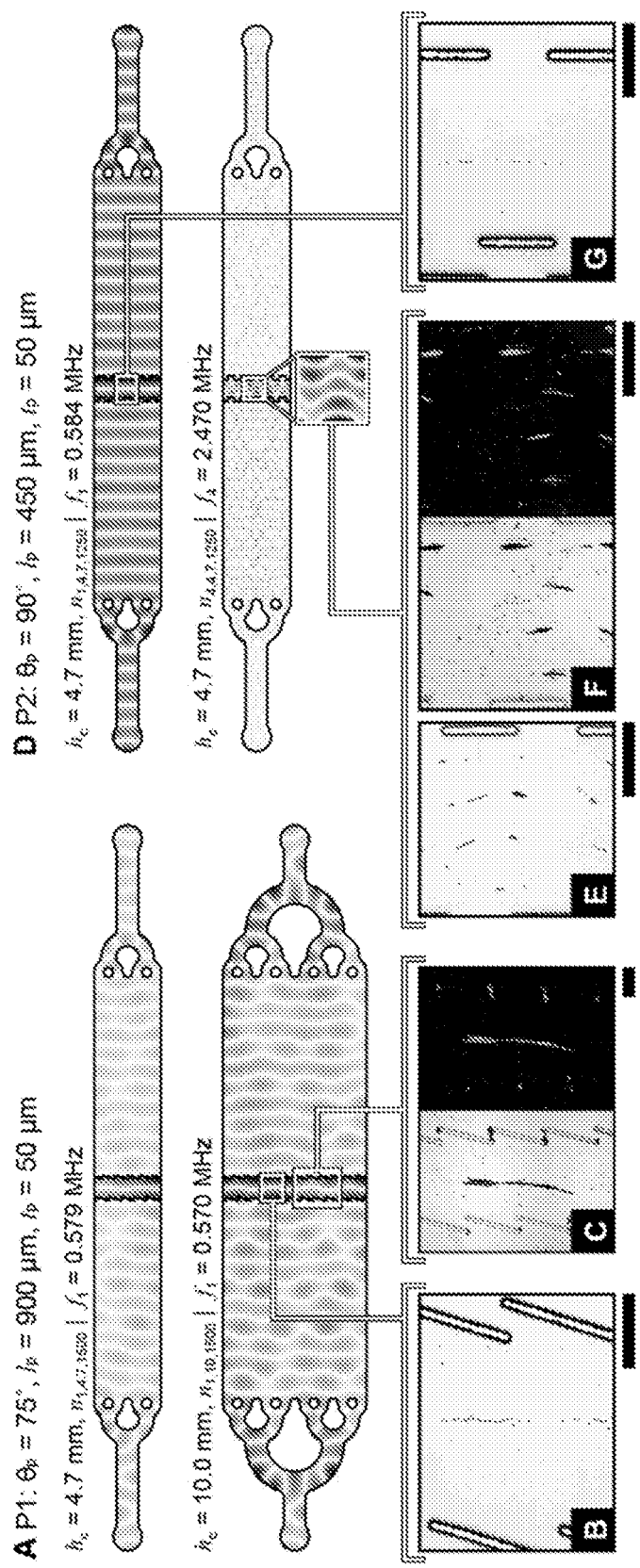
FIG. 13A depicts an exemplary embodiment of a predicted first half-wave resonance corresponding to trapping of targeted particles at a single nodal location perpendicular to the direction of flow for 4.7 mm-wide (f=0.579 MHz) and 10 mm-wide (f=0.570 MHz) channels with slanted pillars, in accordance with the present disclosure.
FIG. 13B depicts an exemplary embodiment of focusing of 20 μm PS beads relative to 5 μm beads along the centerline of the parallel array of slanted pillars in a 10 mm-wide channel at the predicted first half-wave frequency of operation, in accordance with the present disclosure.
FIG. 13C depicts an exemplary embodiment of focusing of antibody-decorated 10 μm glass spheres along the centerline of a parallel array of slanted pillars in a 10 mm-wide channel at the predicted first half-wave frequency of operation, in accordance with the present disclosure.
FIG. 13D depicts an exemplary embodiment of a predicted first half-wave resonance (f=0.584 MHz) corresponding to trapping of targeted particles at a single nodal location and fourth half-wave resonance (f=2.470 MHz) corresponding to trapping of particles at four nodal locations perpendicular to the direction of flow for a 4.7 mm-wide channel with lamellar pillars, in accordance with the present disclosure.
FIG. 13E depicts an exemplary embodiment of a pattern of focused 20 μm PS beads (relative to 5 μm beads) at a mode representative of a fourth half-wave resonance for the 4.7 mm-wide channel with lamellar pillars at f=2.450 MHz, in accordance with the present disclosure.
FIG. 13F depicts an exemplary embodiment of a pattern of focused antibody-decorated 10 μm glass spheres at a mode representative of a fourth half-wave resonance for the 4.7 mm-wide channel with lamellar pillars at f=2.450 MHz, in accordance with the present disclosure.
FIG. 13G depicts an exemplary embodiment of focusing of 20 μm PS beads relative to 5 μm beads along the centerline of the parallel array of lamellar pillars in a 4.7 mm-wide channel at the predicted first half-wave frequency of operation, in accordance with the present disclosure.
Figure 14:
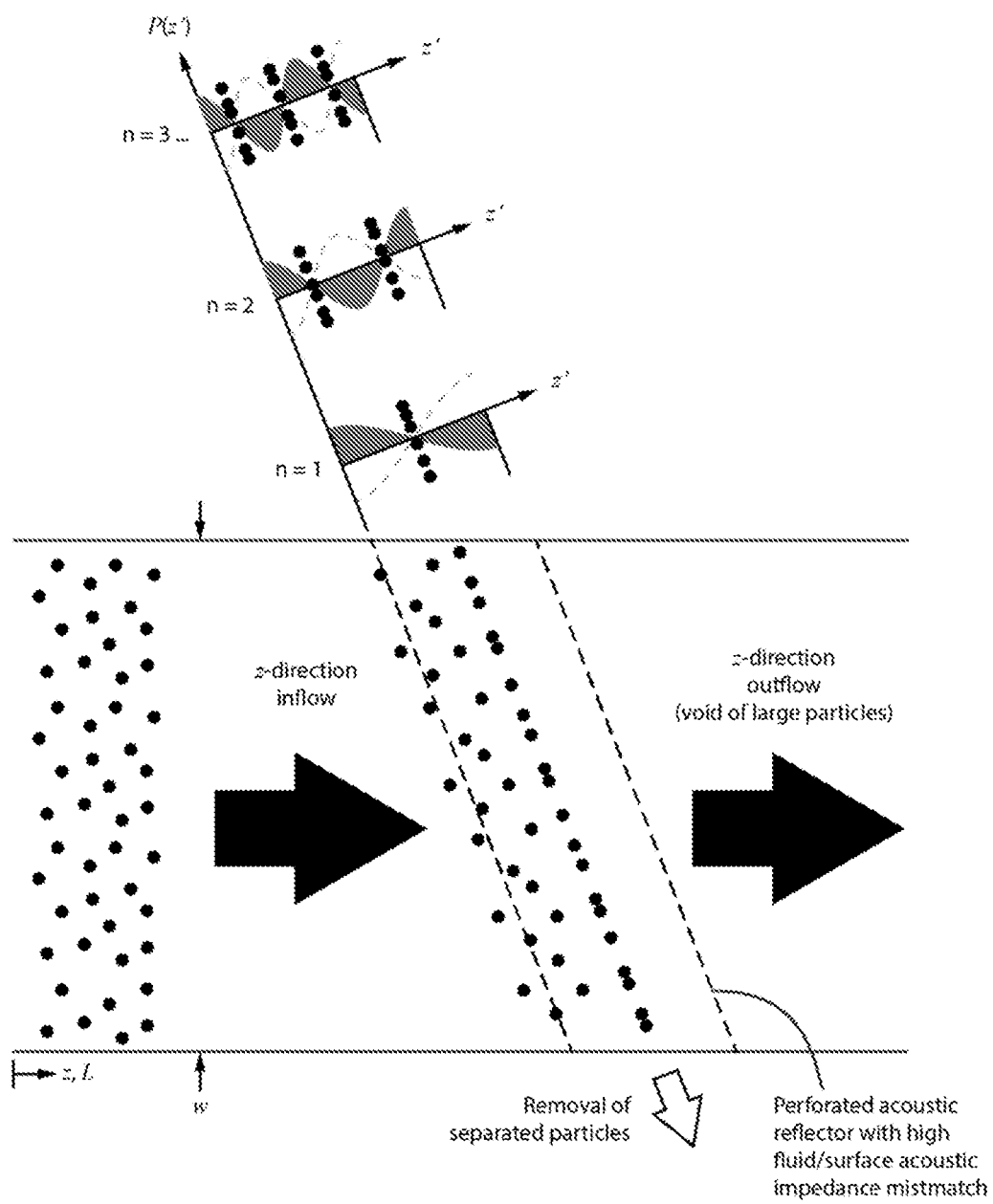
FIG. 14 depicts yet another exemplary embodiment of a system that can perform high throughput acoustophoresis, in accordance with the present disclosure.

For each enrichment structure, the acoustic response of a two-dimensional (2D) representation of the glass channel was first predicted using a frequency domain harmonic response analysis in COMSOL Multiphysics. Potential frequencies of operation were identified for parallel arrays of either slanted (angle of inclination, $\theta_p$=75°) or lamellar pillars. Nominally, both geometries were designed to support single pressure field nodal lines perpendicular to the flow direction at a frequency of 500 kHz (i.e., the gap width between the parallel pillar arrays, $L_x$=1.25-1.5 mm, see FIGS. 12C and 12D). For this analysis, only the fluid (water; density ρ=998 kg m$^{-3}$ and speed of sound c=1481 m s$^{-1}$) domain was considered, and the boundary at the glass channel walls was modeled using a uniform inward normal displacement. FIG. 13A shows the predicted first half-wave resonance corresponding to trapping of targeted particles at a single nodal location perpendicular to the direction of flow for 4.7 mm-wide (f=0.579 MHz) and 10 mm-wide (f=0.570 MHz) channels with arrays of slanted pillars. Similarly, FIG. 13D shows the first half-wave resonance for a 4.7 mm-wide (f=0.584 MHz) channel with lamellar pillars. FIG. 13D also predicts operation at a mode representative of a fourth half-wave resonance for the 4.7 mm-wide channel with lamellar pillars at f=2.470 MHz.

In experiments, inlet/outlet compression ports were used for static loading of particle suspensions. Separations channel chip assemblies were placed in a custom stage insert of an inverted microscope (Axio Observer z.1, Zeiss) for observation of acoustic particle migration. Enrichment frequencies were identified by sweeping transducer actuation over a 50 kHz range about model predicted resonances of interest (33522A, Agilent; 2100L, ENI). FIG. 13B shows focusing of 20 μm PS beads relative to 5 μm beads along the centerline of the parallel array of slanted pillars in a 10 mm-wide channel at the predicted first half-wave frequency of operation (f=0.569 MHz). Similarly, FIG. 13C shows focusing of antibody-decorated 10 μm glass spheres at the same frequency of operation for that device (slanted pillars, 10 mm-wide channel). FIG. 13G shows focusing of 20 μm PS beads relative to 5 μm beads along the centerline of the parallel array of lamellar pillars in a 4.7 mm-wide channel at the predicted first half-wave frequency of operation (f=0.575 MHz). FIGS. 13E and 13F show patterns of focused 20 μm PS beads (relative to 5 μm beads) and antibody-decorated 10 μm glass spheres, respectively, at a mode representative of a fourth half-wave resonance for the 4.7 mm-wide channel with lamellar pillars at f=2.450 MHz. Model and experimental results demonstrate that the ratio of field strength in the enrichment structure to that of the inlet/outlet channels increases with increasing frequency of operation. In all cases observed mode shapes closely matched model predictions validating the understanding of the physics underlying device operation detailed in the present specification.

Those skilled in the art will appreciate that the presently disclosed embodiments teach by way of example and not by limitation. Therefore, the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall therebetween.

What is claimed is:

1. A device comprising:
    a reservoir for receiving a fluid in a flow direction;
    a transducer for generating a pressure field that is not perpendicular to the flow direction of the fluid through the reservoir; and
    at least one acoustic reflective wall located within the reservoir, wherein the wall is not parallel to the flow direction and wherein the wall is perforated to allow fluid flow through the wall in the flow direction.

2. The device of claim 1, wherein at least one node and at least one antinode of the pressure field are within the reservoir.

3. The device of claim 1, wherein the pressure field is an acoustic field.

4. The device of claim 1, wherein the transducer is an actuator.

5. The device of claim 1, wherein the transducer is selected from a piezoelectric transducer, an interdigitated electrode array on a piezoelectric substrate, and combinations thereof.

6. The device of claim 1, wherein the transducer comprises an actuator, an acoustic coupling layer and an isolation layer.

7. The device of claim 6, wherein the acoustic coupling layer and isolation layer have a low ultrasonic attenuation.

8. The device of claim 1, wherein the pressure field is parallel to the flow direction of the fluid.

9. The device of claim 1, wherein a surface of the at least one acoustic reflective wall has a high acoustic impedance mismatch with respect to the fluid.

10. The device of claim 1, wherein the transducer is configured to generate the pressure field between a wall of the reservoir and the at least one acoustic reflective wall.

11. The device of claim 1, wherein the at least one acoustic reflective wall comprises two acoustic reflective walls and wherein the transducer is configured to generate the pressure field between the two acoustic reflective walls.

12. A method of high throughput separation of a plurality of objects, the method comprising:
    receiving a fluid in a flow direction into a reservoir comprising an array of openings on at least one side of the reservoir;
    generating a pressure field that is not perpendicular to the flow of the fluid through the reservoir, wherein at least one node and at least one antinode of the pressure field are within the reservoir; and
    separating the plurality of objects within the fluid, wherein at least a first object is retained within the reservoir and at least a second object is passed from the reservoir through the array of openings.

13. The method of claim 12, wherein the pressure field is an acoustic field.

14. The method of claim 12, wherein the plurality of objects are selected from the group consisting of particles and cells.

15. The method of claim 12, wherein the pressure field is parallel to the flow direction of the fluid.

16. The method of claim 12, wherein generating the pressure field comprises generating the pressure field between perforated acoustic reflector walls located within the reservoir.

17. A device for high throughput separation comprising:
    a reservoir for receiving a fluid in a flow direction comprising an array of openings on at least one side of the reservoir;
    at least one acoustic reflective wall located within the reservoir, wherein the wall is not parallel to the flow direction and wherein the wall is perforated to allow fluid flow through the wall in the flow direction; and
    a transducer configured to generate a pressure field that is not perpendicular to the flow direction of the fluid through the reservoir, wherein at least one node and at least one antinode of the pressure field are within the reservoir.

18. The device of claim 17, wherein the reservoir is a channel or microchannel.

19. The device of claim 17, wherein the pressure field is an acoustic field.

20. The device of claim 17, further comprising an acoustic coupling layer and an isolation layer.

21. The device of claim 17, wherein the pressure field is parallel to the flow direction of the fluid.

22. The device of claim 17, wherein a surface of the at least one acoustic reflective wall has a high acoustic impedance mismatch with respect to the fluid.

23. The device of claim 17, wherein the transducer is selected from a piezoelectric transducer, an interdigitated electrode array on a piezoelectric substrate, and combinations thereof.

24. The device of claim 17, wherein the transducer comprises an actuator, an acoustic coupling layer and an isolation layer.

25. The device of claim 20, wherein the acoustic coupling layer and isolation layer have a low ultrasonic attenuation.

* * * * *